United States Patent [19]

Makovec et al.

[11] 4,320,233

[45] Mar. 16, 1982

[54] DIALKYL ETHER PRODUCTION

[75] Inventors: Donald J. Makovec; Paul D. Hann, both of Bartlesville, Okla.

[73] Assignee: Phillips Petroleum Company, Bartlesville, Okla.

[21] Appl. No.: 232,791

[22] Filed: Feb. 9, 1981

[51] Int. Cl.³ .................... C07C 41/05; C07C 2/60
[52] U.S. Cl. .................................. 568/697; 585/331; 585/723
[58] Field of Search ................ 568/697; 585/331, 723

[56] References Cited

U.S. PATENT DOCUMENTS

| | | | |
|---|---|---|---|
| 3,902,870 | 9/1975 | Rollmann et al. | 44/56 |
| 3,979,461 | 9/1976 | Ancillotti | 260/614 A |
| 4,039,590 | 8/1977 | Ancillotti | 260/614 A |
| 4,071,567 | 1/1978 | Ancillotti | 260/614 |

*Primary Examiner*—Howard T. Mars

[57] ABSTRACT

Dialkyl ether is produced by passing isoolefin, alkanol and diluent through a series of catalyst zones, cooling the effluent between zones and adding isoolefin and/or alkanol between zones.

11 Claims, 1 Drawing Figure

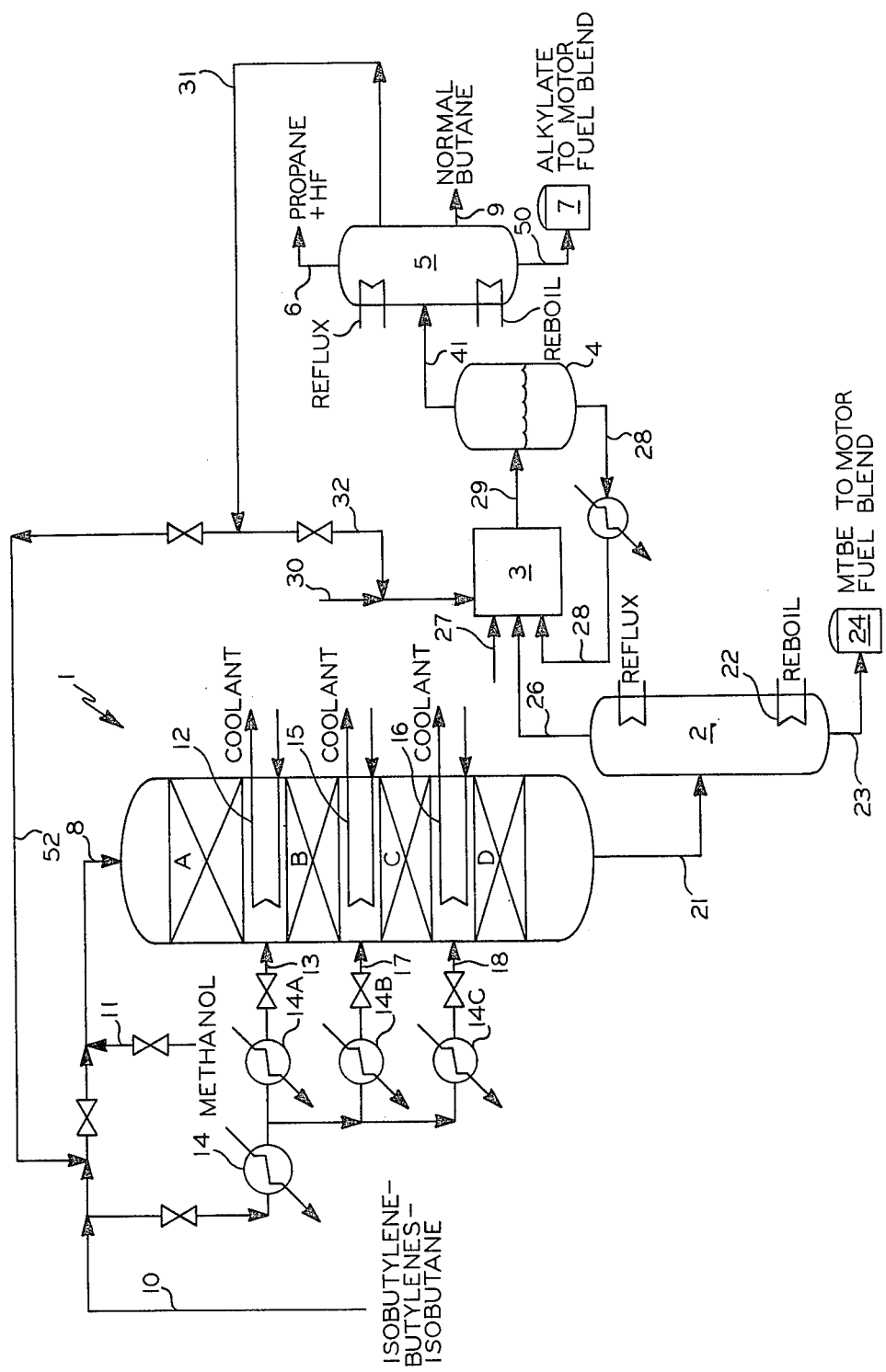

DIALKYL ETHER PRODUCTION

BACKGROUND OF THE INVENTION

Dialkyl ethers such as methyl tert-butyl ether can be produced as is well known in the art by reacting methanol with isobutylene in the presence of an acid ion exchange resin. Such ethers are desirable blending products for the production of high octane gasoline.

In the manufacture of such ethers as methyl tert-butyl ether (abbreviated in the following MTBE) a problem arises which is connected to the strongly exothermic reaction involved. A solution to this problem is suggested by the present invention.

THE INVENTION

It is one object of this invention to provide a new process for the production of dialkyl ethers such as MTBE.

A more specific object of this invention is to provide such a process in which the oligomerization and polymerization of the olefin present in the feedstream which may occur due to the high temperatures, is essentially avoided.

A further object of this invention is to provide a process for converting isobutylene into two high octane blending products for gasoline.

These and other objects, advantages, details, features and embodiments of this invention will become apparent to those skilled in the art from the following description of the invention, the appended claims and the drawing which shows a schematic flow diagram involving both embodiments of this invention, i.e. the production of the dialkyl ether as well as the conversion of isobutylene to two gasoline blending stocks.

In accordance with this invention a process for the production of dialkyl ethers is provided for which can be basically characterized as a multicatalyst zone process with intercooling between the catalyst zones. This intercooling allows to keep the temperature of the reaction relatively constant, to control the conditions rather accurately and to avoid hot spots and hot pockets within large catalyst filled beds.

Thus, in accordance with a first embodiment of this invention a process for the production of an isoalkyl-alkyl ether is provided for. This process involves the exothermic reaction of an isoolefin and an alkanol in contact with a catalyst. The process of this invention comprises passing a stream sequentially through a series of zones containing the catalyst. The stream comprises isoolefin, alkanol and diluent. The effluent of any zone prior to or during the entry of this stream into the next zone is cooled. At least one of isoolefin or alkanol is added to the effluent from one zone prior to or during the entry of the effluent of the next zone. Whereas the basic concept of this invention is applicable to a variety of isoolefins and their reactions with alkanols, it is presently preferred to carry out the process of this invention for the production of MTBE by the reaction of isobutylene and methanol. Other examples of reaction pairs are isopentene and methanol, isobutylene and ethanol, isohexene and methanol, etc.

The interstage cooling in accordance with this invention can be either carried out by indirect heat exchange or by direct heat exchange. In the case of the indirect heat exchange the effluent from one catalyst zone is placed into indirect heat exchange relationship with a coolant such as water or a hydrocarbon stream. In the embodiment involving the direct heat exchange the fluids introduced between the catalyst stages are selected in quantity and temperature so that the stream entering the next catalyst bed comprising the effluent from the preceding catalyst bed as well as the added fluids is at the desired temperature.

The fluids that are added between the catalyst stages are selected from the group consisting of isoolefin, alkanol and diluent. Preferably, a mixture of diluent and isoolefin is added between the stages. If necessary, the fluid added between the stages is cooled prior to the addition.

In the preferred embodiment of this invention the entire quantity of alcohol together with a stream composed of hydrocarbon diluent and some isoolefin is entered into the first stage of the multistage reaction. Between the stages a stream comprising diluent and further isoolefin is added.

Diluents useful in this process emcompass generally the hydrocarbon diluents. Typical examples for such diluents are n-olefins, n-paraffins, isoparaffins and aromatic hydrocarbons. Typical examples of diluents are n-butene, isobutane, n-butane, the pentanes, n-pentene, hexanes, n-hexene and benzene and toluene.

Typical operating conditions for the catalytic conversion process to produce the dialkyl ether are characterized in the following table:

| | |
|---|---|
| Temperature °F., | 130 |
| Pressure PSIG., | 125 (to maintain liquid phase) |
| LHSV, V/V/Hr, | 5 volumes liquid/vol. cat/hr. |

More specifically, for the production of MTBE from isobutylene and methanol the operating conditions will be in the following ranges

| | |
|---|---|
| Temperature °F., | 100 to 200 |
| Pressure PSIG., | 85 to 260 (to maintain liquid phase) |
| LHSV, V/V/Hr., | 0.5 to 20 |

Examples for the catalyst useful in the process of this invention encompass such as amberlyst 15 (U.S. Pat. No. 3,979,461), HF, $H_2SO_4$, $AlCl_3$, etc. (U.S. Pat. No. 3,902,870).

The catalyst in the different beds can be the same catalyst or different catalysts can be used in some of the beds. The bed depth measured along the main flow path can be the same for the individual beds or it can be increasing or decreasing in flow direction. It is presently preferred that the bed depth of the catalyst increases along the flow path in view of the fact that the mass of materials flowing and thus the heat capacity thereof increases from bed to bed. The latter preferred variation is based on the assumption that a constant quantity of reacting material is added in each step between the stages.

It is presently preferred to carry out the process for the production of the dialkyl ethers such as MTBE with an excess of the isoolefin so that the effluent from the last catalyst zone is substantially free of alkanol. The term "excess" refers to the stoichiometric ratio of the total quantity of isoolefin and the total quantity of alkanol employed.

In accordance with a further embodiment of this invention there is provided a process to convert an isobutylene feedstream into two high octane gasoline blending materials. This process uses an excess isobutylene stream and converts this stream together with a lower alcohol such as methanol into a dialkyl ether such as MTBE as described. The final stream produced is substantially free of the alkanol. This stream of this first operation is separated into a dialkyl ether stream and a butenes-isobutane containing stream. This separation advantageously is done in a fractionation column. The butenes-isobutane containing stream thereafter is contacted with an olefin, e.g., isobutylene-butenes and an HF alkylation catalyst in an alkylation zone to produce an alkylation mixture. This alkylation mixture after reaction is separated into a catalyst phase and a hydrocarbon phase. From the hydrocarbon phase an alkylate stream is separated whereas the catalyst phase is recycled to the alkylation zone. This process thus yields a lower alkyl-tertiary butyl ether and alkylate as two products of the process from which both are useful high octane gasoline blending components.

The typical olefins used in the alkylation step are propylene and/or butylene. The alkylation step as such is well known in the art and is for instance described in U.S. Pat. No. 3,233,007. The disclosure of this patent is incorporated herein by reference.

The following description of the drawing illustrates a preferred combined process. The apparatus schematically shown in the drawing will be described in the following in connection with the production of MTBE and an alkylate from isobutylene. Into an MTBE reactor 1 isobutylene is introduced from a line 10. The stream in line 10 in addition to isobutylene also contains diluent such as normal butenes, isobutane and normal butane. A portion of the isobutylene stream 10 is introduced into the top of the reactor 1. A stream of alcohol such as methanol is introduced also into the top of the MTBE reactor 1 from line 11. Inside of the MTBE reactor 1 a plurality of catalyst beds, usually 2 to 8 catalyst beds are arranged. The catalyst beds four of which are shown in the drawing, have been labeled A, B, C and D.

The mixture of isobutylene, methanol and diluent is contacted with the first catalyst bed A under reaction temperature conditions which include a top temperature of 120° F. and a bottom temperature of 140° F. for the catalyst bed A. This catalyst bed A can be filled with an acidic ion exchange resin such as amberlyst 15. Between the first and second catalyst A and B an indirect heat exchanger 12 is arranged for cooling the effluent from the first catalyst bed A. Part of the isobutylene stream from line 10 is introduced between catalyst beds A and B via line 13. This side stream of isobutylene with diluent has been cooled in a cooler 14 to a temperature of e.g. 125° F. Both the direct heat exchange achieved by the low temperature feed stream 13 and the indirect heat exchanger 12 bring the total stream reaching the catalyst bed B to the desired temperature of e.g. 130° F. Similarly, indirect heat exchangers 15 and 16 are arranged between catalyst beds B and C and respectively C and D. Side streams 17 and 18 of isobutylene and diluent are also introduced between these catalyst beds. Streams 13, 17, and 18 can be sparged into the spaces between the beds for mixing thereof with a bed effluent.

From the MTBE reactor 1 an effluent stream is withdrawn via line 21. This effluent stream contains MTBE, isobutylene, diluent and essentially no methanol. Furthermore, this stream contains only a minimal quantity of polymerized or oligomerized isobutylene.

The product stream from the MTBE reactor 1 is introduced into a fractionator 2 which is reboiled by a reboiler 22. From the bottom of the fractionator 2 an MTBE stream is passed via line 23 to a storage tank 24. The overhead stream withdrawn from the fractionator 2 via line 26 comprises isobutylene and isobutane, and is introduced into an alkylation zone 3 together with an olefin stream, e.g. butene-1; butenes-2; and isobutane, introduced via line 27 and an HF alkylation catalyst stream (cooled and recycled) introduced via line 28. Startup A isobutane, as required, is added via line 30. Recycle isobutane is added by lines 31 and 32. The alkylate effluent from the alkylation reaction zone 3 is passed via line 29 to a settler 4. From this settler 4 the hydrocarbon phase is withdrawn via line 41 and introduced into a fractionator 5. From the fractionator 5 the alkylate product is removed via line 51 to storage tank 7. Recycle isobutane 31 is recovered from fractionator 5 and returned via 32 to alkylation zone 3. Propane along with HF vapor is removed at 6 (for charge to HF stripper, not shown to recover HF and propane); and normal butane vapor is removed at 9. Part of the isobutane from line 31 is passed via line 51 as diluent for reactor 1, ultimately being charged (recycled) to alkylation zone 3 via line 26. HF alkylation catalyst is withdrawn from the settler 4 and passed back into the HF alkylation zone 3 via line 28 and cooler, not shown.

In the following a typical calculated material balance for the various streams is given:

| CALCULATED EXAMPLE | | | | | | | | | |
|---|---|---|---|---|---|---|---|---|---|
| Stream | Pounds/hour | | | | | | | | |
| Component | 10 | 52 | 11 | 8 | 13 | 17 | 18 | 21 | 23 |
| Methanol | — | — | 6.3 | 6.3 | — | — | — | 0.11 | —(a) |
| Isobutylene | 11.8 | — | — | 2.95 | 2.95 | 2.95 | 2.95 | 0.97 | — |
| Isobutane | 47.0 | 293 | — | 304.75 | 11.75 | 11.75 | 11.75 | 340.0 | — |
| Normal Butenes | 30.6 | — | — | 7.65 | 7.65 | 7.65 | 7.65 | 30.6 | — |
| Normal Butane | 10.6 | 29 | — | 31.65 | 2.65 | 2.65 | 2.65 | 39.6 | — |
| Alkylate | — | — | — | — | — | — | — | — | — |
| MTBE | — | — | — | — | — | — | — | 17.02 | 17.02 |
| TOTAL | 100.0 | 322 | 6.3 | 353.3 | 25.00 | 25.00 | 25.00 | 428.3 | 17.02 |

| Stream | Feed to | | | | | | | | |
|---|---|---|---|---|---|---|---|---|---|
| Component | 26 | 27 | 32 | 3 | 41(c) | 9 | 50 | 31 | 30 |
| Methanol | —(a) | — | — | — | — | — | — | — | —(b) |
| Isobutylene | 0.97 | 47.2 | — | 48.17 | — | — | — | — | — |
| Isobutane | 340 | 188 | 2177 | 2705 | 2470 | — | — | 2470 | 90% |
| Normal Butenes | 30.6 | 122.4 | — | 153.0 | — | — | — | — | — |
| Normal Butane | 39.6 | 42.4 | 218 | 300.0 | 300 | 40 | 13 | 247 | 10% |
| Alkylate | — | — | — | — | 436.17 | — | 436.17 | — | — |
| MTBE | — | — | — | — | — | — | — | — | — |

| CALCULATED EXAMPLE | | | | | | | | |
|---|---|---|---|---|---|---|---|---|
| -continued | | | | | | | | |
| TOTAL | 411.17 | 400.0 | 2395 | 3206.17 | 3206.17 | 40 | 449.17 | 2717 — |

(a) Methanol, when present, is removed by such as water wash and drying, or by such as molecular sieve. Use of higher ratio of isobutylene-to-methanol in final reactor D minimizes methanol that is yielded unreacted, not illustrated in the drawing.
(b) Used on startup to attain isobutane-to-olefin ratio in alkylation.
(c) May have about 5 percent propane (not used in example to simplify calculations made).

| OPERATING CONDITIONS | | | | |
|---|---|---|---|---|
|  | Reactor A | Reactor B | Reactor C | Reactor D |
| Temperatures, °F. | | | | |
| Inlet of Bed | 125 | 125 | 125 | 125 |
| Outlet of Bed | 130 | 130 | 130 | 130 |
| Pressures, PSIG | | | | |
| Inlet of Bed | 130 | 128 | 126 | 124 |
| Outlet of Bed | 128 | 126 | 124 | 122 |
| Liquid Hourly Space Velocity | | | | |
| Vol. Flow/Vol. Cat./Hr | 5 | 5 | 5 | 5 |
| Catalyst: | | | | |
| Each Bed | Amberlyst 15 | Amberlyst 15 | Amberlyst 15 | Amberlyst 15 |
|  |  | Fractionator (2) | Fractionator (5) | Alkylation Zone (3) |
| Temperatures, °F. | | | | |
| Top, |  | 129 | 140 | × |
| Bottom, |  | 254 | 275 | × |
| Average, |  | × | × | 90 |
| Pressure, PSIG., |  | 95(reboiler) | 115 | 160 |
| Isobutane/Olefin Vol. Ratio |  | × | × | 12:1 |
| HF/Hydrocarbon Vol. Ratio |  |  |  | 4:1 |
| Catalyst | | | | |
| HF |  | × | × | 92.0 |
| H$_2$O |  | × | × | 2.0 |
| Acid Soli Oil |  | × | × | 3.0 |
| Hydrocarbon(iC$_4$) |  | × | × | 3.0 |

In accordance with this invention a process has been provided which allows the production of dialkyl ethers from isoolefin and alkanols without any significant isoolefin oligomerization or polymerization. This is achieved by subdividing the reaction zone into a plurality of catalyst zones and cooling the stream between the catalyst zones as well as by feeding part of the feedstock between the catalyst zones into the reactor. As a general rule, the temperature rise within one catalyst zone from the input temperature to the output temperature will be at/or below about 5° F.

Reasonable variations and modifications which will become apparent to those skilled in the art can be made in this invention without departing from the spirit and scope thereof.

We claim:

1. A process for producing a dialkyl ether by exothermic reaction of isoolefin and alkanol in contact with catalyst, said process comprising
   (a) passing a stream comprising isoolefin, alkanol and diluent sequentially through a series of zones containing said catalyst,
   (b) cooling the effluent of any zone prior to or during the entry thereof into the next zone,
   (c) adding at least one of isoolefin and alkanol to the effluent from one of said zones prior to or during the entry thereof into the next zone.

2. A process in accordance with claim 1 wherein said cooling is achieved by indirect heat exchange.

3. Process in accordance with claim 1 wherein said series of zones is a plurality of catalyst beds in one reactor and wherein said cooling is achieved by interstage cooling using indirect heat exchange means.

4. Process in accordance with claim 1 wherein said cooling is achieved by direct heat exchange.

5. Process in accordance with claim 4 wherein said direct heat exchange is carried out by adding prior to or during the entry of the effluent of one zone into the following zone fluids comprising diluent and isoolefin and/or alkanol in quantities and at temperatures to said effluent to achieve the desired temperature of the combined fluids entering said zone.

6. A process in accordance with claim 1 wherein the total quantity of isoolefin employed in the process exceeds stoichiometrically the total quantity of alkanol employed so that the effluent from the last zone is substantially free of alkanol.

7. Process in accordance with claim 6 wherein the total quantity of isoolefin employed is introduced into the first zone and wherein fractions of the total quantity of alkanol employed are introduced into the first zone and into the following zones.

8. A process in accordance with claim 1 wherein said isoolefin is isobutylene, said alkanol is methanol and said catalyst is an acidic ion exchange resin.

9. A process to convert isobutylene into two high octane gasoline blending materials comprising
   (A) producing MTBE by
      (a) passing a stream comprising isobutylene, methanol and hydrocarbon diluent containing isobutane sequentially through a series of zones containing a catalyst for converting isoolefin and alkanol to dialkyl ether, (b) cooling the effluent of any zone prior to or during the entry thereof into the next zone, (c) adding at least one of isobutylene and methanol to the effluent from one zone prior to or during the entry thereof to the next zone, with the proviso that the total quantity of isobutylene employed in the multizone process exceeds stoichiometrically the total quantity of methanol employed so that the effluent from the last zone is substantially free of methanol, (d) passing the effluent from the last zone to a fractionation zone to yield a bottom stream containing MTBE and an overhead stream containing isobutylene and isobutane, (B) producing a high octane alkylate by (a) introducing said overhead stream as at least a portion of the isoolefin feedstock to an HF alkylation zone, (b) introducing an olefin and HF alkylation catalyst to said HF alkylation zone to produce an alkylation mixture, (c) withdrawing after reaction said alkylation mixture and separating it into a catalyst phase and a hydrocarbon phase, and (d) recovering alkylate as the second product of the process from said hydrocarbon phase.

10. Process in accordance with claim 9 wherein said olefin is selected from the group consisting of propylene, butylene and mixtures thereof.

11. Process in accordance with claim 9 wherein said catalyst phase is recycled to said HF alkylation zone.

* * * * *